United States Patent [19]
Macur

[11] 3,957,613
[45] May 18, 1976

[54] MINIATURE PROBE HAVING MULTIFUNCTIONAL ELECTRODES FOR SENSING IONS AND GASES

[75] Inventor: Robert A. Macur, Milwaukee, Wis.

[73] Assignee: General Electric Company, Schenectady, N.Y.

[22] Filed: Nov. 1, 1974

[21] Appl. No.: 519,793

[52] U.S. Cl. .......................... 204/195 M; 128/2 E; 204/195 R; 204/195 P
[51] Int. Cl.² ........................................ G01N 27/46
[58] Field of Search ............ 204/195, 1 T; 128/2 E, 128/2.1 E; 324/29

[56] References Cited
UNITED STATES PATENTS

| | | | |
|---|---|---|---|
| 3,794,575 | 2/1974 | Niedrach et al. | 204/195 P |
| 3,835,013 | 9/1974 | Grubb et al. | 204/195 P |

Primary Examiner—G. L. Kaplan
Attorney, Agent, or Firm—Ralph G. Hohenfeldt; Fred Wiviott

[57] ABSTRACT

A miniature probe for simultaneously sensing ion concentrations and partial pressures of gases in a sample comprises plural sensing electrode systems at least one of which is surrounded by an electrolyte and a gas permeable or ion permeable diffusion barrier. The systems are united structurally to form a probe. Various potentials are measured between components of the electrode systems which potentials are indicative of ion and gas concentrations in the sample in which the probe is inserted. Potentials between certain of the internal probe electrodes and external electrodes are indicative of other ions or gases. Partial pressures of oxygen and carbon dioxide gases and concentrations of hydrogen, bicarbonate ions and other cations and anions are typical constituents of a sample that can be determined with the probe.

15 Claims, 1 Drawing Figure

U.S. Patent May 18, 1976  3,957,613
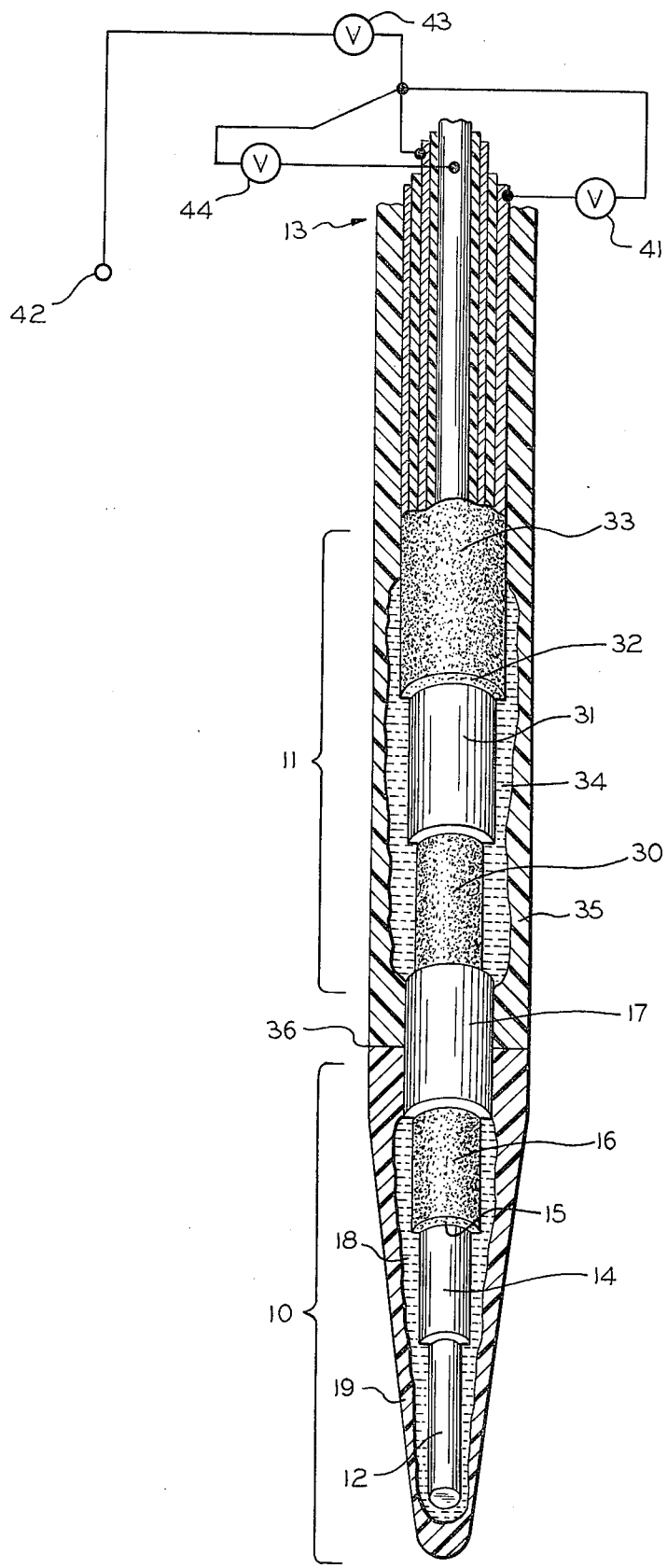

3,957,613

MINIATURE PROBE HAVING MULTIFUNCTIONAL ELECTRODES FOR SENSING IONS AND GASES

BACKGROUND OF THE INVENTION

This invention relates to a probe comprising multifunctional electrodes for simultaneous determination of the concentrations of specific ions and gases in a fluid sample. The invention is primarily exemplified in a probe for determining the partial pressures of carbon dioxide and oxygen gases and pH or hydrogen ions and bicarbonate ions in a fluid sample where the term "fluid" means liquid or gaseous.

The probe to be described herein is intended for analysis of various fluid samples but it is particularly useful for analyzing blood in a blood vessel since the probe is small and can perform multiple analytical functions with only a single invasion of the vessel.

There are probes in the prior art for sensing a single constituent such as pH or hydrogen ions and carbon dioxide and oxygen partial pressures, respectively, in a fluid sample. Probes for measuring pH are described in U.S. Pat. Nos. 3,671,414, 3,709,810 and 3,726,777. Carbon dioxide probes are described in U.S. Pat. Nos. 3,673,069, 3,705,088, 3,709,812 and 3,719,576. A probe for measuring oxygen is described in U.S. Pat. No. 3,839,178. Methods for making probes are described in U.S. Pat. No. 3,798,750. These patents are assigned to the assignee of the present application.

SUMMARY OF THE INVENTION

The present invention involves an improved miniature multifunctional probe which is particularly useful for in vitro and in vivo analysis of body fluids and is generally useful for measuring gaseous and ionic components of biologically active atmospheres or solutions such as are encountered in environmental control, sewage being an example, and food processing and still other applications.

A main object of the invention is to provide a miniature multifunctional probe for sensing sample constituents simultaneously such as oxygen, carbon dioxide and specific ions such as hydrogen and bicarbonate ions and other ions for which the probe is particularly designed.

Another object is to provide a probe which is unitary and small so as to be particularly well adapted for indwelling use in a blood vessel to derive analytical information with only a single invasion of the blood vessel.

In general terms, an illustrative embodiment of the probe comprises a central wire of tantalum, tungsten or molybdenum. A tip portion of this wire is uninsulated and a portion adjacent the tip is insulated and spaced from a surrounding silver-silver halide reference electrode. The two electrodes are surrounded by a suitable electrolyte which is encapsulated in a membrane or diffusion barrier that is permeable to both oxygen and a selective ion such as hydrogen ions to enable pH measurements. This electrode is sensitive to oxygen gas and hydrogen ions. A second electrochemically independent electrode system is axially spaced from the first one and is built around the central wire. The second system has a silver-silver halide reference electrode. The reference electrode is in insulating spaced relationship to another electrode comprised of iridium or palladium having a coating comprised of an oxide of the selected metal. This electrode is sensitive to carbon dioxide. The second electrode system is surrounded by an electrolyte which is encapsulated in a membrane which is permeable at least to carbon dioxide. Electrically conductive elements extend out of the probe to enable making potential measurements between the various electrodes in the probe and between internal electrodes and external auxiliary electrodes. The measured potentials are related to the levels of the ions and gases that the probe is adapted to sense in the sample in which the probe is inserted.

How the above mentioned and other more specific objects of the invention are achieved will be evident in the more detailed description of an illustrative embodiment of the new probe which will now be set forth in reference to the drawing.

DESCRIPTION OF THE DRAWING

The single FIGURE is a partial sectional view of a probe illustrating the electrode systems thereof and further showing diagrammatically the means for measuring potentials which are indicative of the concentrations of sample constituents.

DESCRIPTION OF A PREFERRED EMBODIMENT

In the drawing, the distal end of the probe comprises an electrode system 10 for sensing the partial pressure of oxygen and hydrogen ion concentration or pH in a fluid sample. The axially adjacent electrode system 11 is for sensing the partial pressure of carbon dioxide in a fluid sample into which the probe is inserted. One or the other of the systems may be modified or electrode systems, not shown, may be added to adapt the probe for sensing other gases or ions.

Electrode system 10 comprises a central wire 12 which may be molybdenum, tantalum or tungsten, preferably the latter. Central wire 12 may also comprise a metallic or non-metallic substrate filament on which one of these metals is coated to provide an electrochemically active tip. The uninsulated distal end tip of wire 12 is an oxygen sensitive electrode. In the instant embodiment, the tungsten wire 12 is substantially coextensive with the length of the probe which would ordinarily have suitable electrical connectors, not shown, at its proximal end 13 to allow for external measurement of potentials between electrodes in systems 10 and 11.

Central tungsten wire 12 has an insulating coating 14 surrounding it. This coating extends to proximal end 13 of the probe. Surrounding insulating layer 14 is a silver tube 15 whose outside periphery is coated with silver halide other than fluoride, such as silver chloride 16 to serve as a reference electrode. Tube 15 could be non-metallic or of a metal other than silver which is coated with an imperforate layer of silver that merely serves as a substrate for the silver halide electrochemically active region of electrode 15. Electrode tube 15 extends to the proximal end 13 of the probe.

Tubular silver electrode 15 and, particularly the exposed silver halide coated region 16 is isolated electrically from the remainder of the structure by a tightly surrounding insulating tube 17 which may be polytetrafluorinated ethylene such as that known by the DuPont Company trademark, Teflon, for example. Other good insulating materials may be substituted. Tungsten wire 12 tip electrode, insulator 14 and the silver-silver halide reference electrode 16 are contacted by an electrolyte 18. The electrolyte is captured in a membrane or diffusion barrier 19 which, in the instant example, is permeable to hydrogen ions and oxygen. The electrode system comprised of tungsten wire 12, silver-silver halide reference electrode 16, electrolyte 18 and diffusion barrier 19 cooperate to produce externally measurable potentials indicative of the partial pressure of oxygen in a sample surrounding the diffusion barrier. A potential measured between internal silver halide reference electrode 16 and an external electrode 42, shown near the proximal end and also in ionic communication with the sample permits obtaining the value of the hydrogen ion concentration or pH of the sample as will be described more fully hereafter. Thus, electrode system has the active components for producing potentials indicative of oxygen partial pressure and pH.

Electrode 12, whether it be made of tantalum, molybdenum or tungsten, is preferably in the form of a wire 10 to 12 mils in diameter if the probe is to be used for measuring small samples or for invasion of a blood vessel but this electrode and the other electrodes too may be larger and have any suitable configuration for other applications. Insulation layer 14 may be Alkanex polyester resin lacquer which is applied by dipping while electrode tip 12 is masked. Besides Teflon, insulator 17 may comprise the copolymer identified by the trademark Tefzel which, like Teflon is owned by the DuPont Company. Tefzel is a copolymer of Teflon and polyethylene. Other suitable insulating materials for tubular insulating sleeve 17 are polypropylene, polyethylene, glazed paint, epoxy and Mylar which is a trademark of DuPont Company.

Electrolyte 18 preferably comprises 0.15M halide salt, excluding fluoride, in aqueous solutions and a buffer such as potassium biphthalate to buffer the electrolyte preferably at about pH 5. The electrolyte should be above pH 4.8 and below pH 5.4. Any well known buffer such as borate and phosphate may be used but the concentration of the buffer should be commensurate with buffer capacity desired or, with the desired life expectancy of the sensor. The electrolyte is preferably thickened to facilitate deposition and to simplify applying the diffusion barrier 19 which is also done by dipping in a solution containing a volatile solvent. The molarity, M, of the dissolved halide salt, which may, for example, be potassium chloride or sodium chloride is not extremely critical insofar as the involved electrochemical reactions are concerned but in a sensor that is to be used in body fluids such as blood, it is desirable to have an osmolarity of about 300 milliosmoles since this makes the electrolyte substantially isotonic, or more aptly, isoosmotic with the electrolytes and non-electrolytes in the body fluid. Making the electrolyte isoosmotic minimizes the tendency for bidirectional migration of water between the body fluid sample and the electrolyte inside of diffusion barrier 19. More information on the oxygen responsive electrode system 10 is obtainable from U.S. Pat. No. 3,839,178, owned by the assignee of this application, which is incorporated herein by reference.

Suitable diffusion barriers 19 are preferably made in accordance with U.S. Pat. No. 3,743,588 to J. F. Brown, Jr. et al, which patent is assigned to the assignee of the present application and is incorporated herein by reference. A barrier made in accordance with the examples in the patent is permeable to oxygen and may be made permeable to hydrogen ions and other cations by including the desired ion carriers. For hydrogen permeability the barrier, in accordance with the patent, may comprise a hydrophobic elastomer polymer with a dielectric constant of from 4 to 13 and a $H^+$ ion carrier which is an uncoupler known to uncouple oxidative phosphorylation in mitochondria and choloroplast, the uncoupler being rendered hydrophilic and lipophilic.

The carbon dioxide sensing electrode system 11 will now be described. Its components have counterparts in U.S. Pat. No. 3,719,576, dated Mar. 6, 1973 in the name of the instant inventor and assigned to the assignee of this application. This patent is incorporated herein by reference.

In the FIGURE, the carbon dioxide sensing electrode system 11 comprises a silver-silver halide reference electrode 30 which is a continuation of silver tube 15 and its silver halide coating 16. Reference electrode 30 is made electrically independent of electrode 16 by insulating layer 17 which may be composed of any of the materials mentioned above for insulator 14. The silver tube 15 bearing silver halide layer 30 portion is surrounded by an insulating tube 31 which may be a tube or any of the materials mentioned above for use as insulator 17. Insulating tube 31 is surrounded by a palladium tube 32 which has its end and its periphery coated with palladium oxide 33 to make it an electrochemically active electrode. As is evident, the palladium-palladium oxide electrode 33 and silver halide reference electrode 30 are electrically isolated from each other by insulator 31. The active coated regions of electrodes 30 and 33 and insulator 31 are mutually contacted by an electrolyte 34 which provides a conductive path between electrodes 30 and 33. Electrolyte 34 is encapsulated in a diffusion barrier 35 which, in this example, is preferably permeable to carbon dioxide gas and impermeable to hydrogen ions. At least the palladium substrate 32 extends toward the proximal end 13 of the probe where suitable electrical connections are made for measuring potentials between the palladium oxide active region 33 and reference electrode active region 30. The potentials are representative of carbon dioxide partial pressure in the sample in which the probe is immersed.

Iridium and iridium oxide may be substituted for palladium 32 and palladium oxide 33, respectively, in carbon dioxide electrode system 11. Forming of palladium and iridium oxide electrodes which are pH and carbon dioxide sensitive is described in U.S. Pat. No. 3,719,576 mentioned earlier.

Electrolyte 34 may comprise an aqueous solution of 0.001 to 0.15 molar sodium bicarbonate with sufficient sodium chloride in the solution to make it substantially isoosmotic with the sample being measured. The electrolyte is preferably in a thickened solution. Starch or methyllated cellulose may be used for thickening. The carbon dioxide permeable diffusion barrier may be organo-polysiloxane-polycarbonate block copolymer which is described in U.S. Pat. No. 3,189,622 and it may be deposited on the thickened electrolyte by dipping. This patent is incorporated herein by reference. The manner of doing this is set forth in the above cited U.S. Pat. No. 3,719,576 which is incorporated herein by reference.

The carbon dioxide permeable ion-impermeable diffusion barrier 35 may extend from its junction line 36 with oxygen and hydrogen ion permeable barrier 19 to the proximal end of the probe. It is preferable to merely extend membrane 35 continuously to the proximal end 13 of the probe since it only involves dipping the probe deeper into the solution that forms diffusion barrier 35. This eliminates the need for a separate insulator proximally of electrode system 11 since the diffusion barrier material mentioned hereinabove is insulating.

Potentials between various internal and external electrodes in the probe may be measured as indications of the concentration of ions, such as hydrogen ions, and partial pressures, such as the partial pressure of oxygen and carbon dioxide, in the sample. All measurements are made with suitably calibrated high input impedance voltmeters. An exemplary measuring system is shown in U.S. Pat. No. 3,710,778 to F. L. Cornelius, dated Jan. 16, 1973. This patent is assigned to the assignee of this application and is incorporated herein by reference. The measuring circuits are illustrated schematically herein. The meter for measuring the partial pressure of carbon dioxide is marked 41. It is connected for measuring the potential between the palladium-palladium oxide electrode 33, which is internal to the carbon dioxide electrode system 11, and silver halide electrode 31 which is also internal to electrode system 11.

The concentration of bicarbonate ions in a sample in which the probe is inserted is preferably calculated, based on knowledge of the carbon dioxide and pH levels. A potential corresponding with bicarbonate ion concentration could be measured, not shown, between silver halide electrode 30, which is internal to the carbon dioxide electrode system 11, and an external reference electrode 42. Reference electrode 42 is a conventional silver-silver chloride electrode which contacts the sample externally of the probe. When the probe is in a blood vessel for measuring bicarbonate ion concentration, reference electrode 42 is preferably fastened to contact the subject's skin or a fluid column in the cannula which contains the pH portion. If the probe is being used in an in vitro sample, reference electrode 42 may be immersed or otherwise in direct ionic communication with the aqueous sample solution.

When the partial pressure of carbon dioxide is known from the carbon dioxide measurement discussed above, the bicarbonate ion concentration can be calculated with the Henderson-Hasselbalch equation as follows:

$$pH = pKa + \log \frac{(HCO_3^-)}{.0303 \, pCO_2}$$

where:
  $pCO_2$ is partial pressure of carbon dioxide expressed in torrs;
  $HCO_3^-$ is concentration of bicarbonate ion in milliequivalents per liter; and
  pKa is the same as the negative logarithm of the dissociation constant which, in this case, has a value of 6.1 and is dimensionless.

Hence, when any two of the pH, carbon dioxide or bicarbonate are known, the other can be calculated.

A potential indicative of the partial pressure of oxygen in the sample is measured between tungsten electrode 12, which is internal to the oxygen electrode system 10, and the silver-silver halide electrode 16 which is also internal to oxygen electrode system 10. Note that silver halide electrode 16 in the oxygen system 10 and silver halide electrode 30 in the carbon dioxide system 11 are actually common electrodes insofar as making external connections are concerned since the silver tube 15 having the halided regions 16 and 31 extends to the proximal end 13 of the probe for accessibility to external connections. They are independent insofar as internal activity is concerned. The potential indicative of partial pressure of oxygen is measured with a high input impedance voltmeter 44.

The measurement of pH is made with a high input impedance voltmeter 43 connected effectively between silver halide electrode 16, which is internal to the oxygen electrode system 10, and a body contacting or immersible silver-silver chloride reference electrode 42. Recall that electrolyte 18 in the oxygen electrode system 10 is buffered at pH 5. Hence, the pH of the oxygen electrode will not change when carbon dioxide in the sample varies in the normal physiological range of 10 to 100 torr. In response to pH changes, the potential across oxygen gas and hydrogen ion permeable membrane 19 will change only on the outside of membrane 19. Thus, it is the potential between the outside of membrane 19 and external reference electrode 42 that is actually measured as indicative of pH.

A typical procedure for making a multifunctional probe such as is depicted in the drawing is as follows:

A tungsten, molybdenum or tantalum core wire 12 is subjected to surface cleaning with a degreasing solvent such as methylene chloride. The wire, except for its distal and proximal tips is dipped in an insulating resin containing a volatile such as Alkanex polyester resin lacquer. The coated wire is heated at a temperature of 100°C to evaporaate the solvent and then to 200°C to cross-link the coating. This coating step is repeated several times. An alternative to insulating the wire 12 with a resin lacquer is to insert the wire in a tube such as the Teflon tube 14. In such case it is desirable to first apply a sealant such as self-curing silicone sealant on the wire and slip the tube 14 over it. The purpose of the sealant is to prevent fluid from the electrolyte moving along the wire by capillarity. Any of the heat shrinkable resins such as polyethylene, Teflon or polyvinyl chloride may also be used.

The most convenient method for forming the silver halide surfaces 16 and 30, if a silver tube 15 is not used, is to dip the components thus far described into lacquer containing finally divided silver particles. The lacquer may employ Alkanex polyester resin lacquer as a binder for the silver particles. Only one coat is applied. The silver coating adjacent the first insulating region 14 in the oxygen-pH electrode system 10 and the silver halide region 31 in the carbon dioxide electrode system 11 are halided simultaneously in situ anodically at a current of 0.5 milliamperes using 0.1N HCl bath with a platinum electrode serving as the counter electrode. Forming the silver chloride regions 16 and 30 as just described is accomplished after insulating regions 17 and 31 are created in the individual electrode assemblies. Insulating portions 17 and 31 may be formed by painting a band of Alkanex resin, preferably two coats on the silver tube. Insulating region 31 should extend to the proximal end 13 of the probe.

A palladium or iridium tube 32 is then slipped over insulating portion 31 so as to terminate in the carbon dioxide electrode system 11 as depicted in the drawing. Before tube 32 is installed, that portion which is contiguous with electrolyte 34 in the carbon dioxide electrode system 11 must have a coating of palladium oxide 33 on its surface. This is done prior to assembly by dipping the end of tube 32 into 50 weight percent sodium hydroxide in water, heating the tube to 800°C in air for 20 minutes, cooling the tube, rinsing it in distilled water and finally drying it in air.

A coating of thickened electrolyte 34 is then applied for the carbon dioxide electrode system 11. The prove is then, with its proximal end 13 down, dipped into a solution of polysiloxypolycarbonate block copolymer in methylene chloride. The methylene chloride evaporates. The resulting outer sheath 35 is then continuous to both ends of the probe. This coating is insulating but it does provide a diffusion barrier layer 35 for diffusion of carbon dioxide into and out of electrolyte 34. The barrier 35 is then cut with a blade circumferentially about line 36 and the barrier is stripped from the probe from insulator 17 to the tip. The tip end including silver halide region 16, insulator 14 and tungsten tip 12 are then rinsed and dried.

Next the distal tip oxygen-pH sensing electrode system 10 is coated with thickened electrolyte 18. This is followed by dipping the distal end in a suitable solution for forming the membrane or diffusion barrier 19 which is permeable to oxygen gas and hydrogen ions. A suitable diffusion barrier material may be selected from U.S. Pat. No. 3,743,588 issued to J. F. Brown, Jr. et al. Reference is made to examples 1–9 in that patent which discloses how to prepare for casting a film or diffusion barrier by dissolving a block copolymer that includes ionic carriers in methylene chloride solution. For the purposes of the instant case, the distal end tip is dipped in this solution after electrolyte 18 is applied and the methylene chloride is allowed to evaporate so that an imperforate diffusion barrier 19 is formed.

After the foregoing steps are completed, electrical terminations or connections are formed in the vicinity of the proximal ends as in U.S. Pat. No. 3,719,576 which discloses a carbon dioxide sensor and was issued on Mar. 6, 1973 to the inventor of this application.

In the illustrative embodiment, the active and insulating elements of the electrode systems are arranged axially with respect to each other so as to provide an elongated thin probe that is especially suitable for blood vessel invasion. The probe is also suitable for isolated samples of limited volume. However, those skilled in the art will appreciate that as long as the essential components are present, they may be variously sized and arranged as long as the electrode systems are isolated from each other. Those skilled in the art will appreciate that additional electrode systems such as for measuring other specific ions may also be arranged coaxially along the body of the probe so that oxygen and carbon dioxide gases and hydrogen ions as well as other specific ions may be sensed during a single invasion of a blood vessel. When the probe is used in a blood vessel, of course, it is inserted through a cannula, not shown.

It should also be evident that the carbon dioxide sensing electrode system 11 could be at the tip of the probe in place of oxygen-pH sensing electrode system 10. In such case the central wire would be palladium-palladium oxide and, of course, the diffusion barriers and electrolytes would be interchanged. A tungsten tube would also be substituted for the palladium tube to adapt electrode system 11 for oxygen-pH sensing.

An electrode system 10 has been described in considerable detail to illustrate one system for sensing ions, such as the hydrogen ion, and gases, such as oxygen in a probe that also has a separate gas sensing electrode system 11 and that facilitates determination of another ion concentration such as bicarbonate ions. Other ion selective systems may also be combined with gas sensing systems to sense hydrogen, potassium, sodium, calcium magnesium and ammonium cations and chlorine, lactate and pyruvate anions which are presently believed to be biologically significant anions and cations. Suitable electrodes, electrolytes and diffusion barriers must be used. Information on additional systems may be obtained from the book: "Ion-Selective Electrodes", edited by Richard A. Durst, published by National Bureau of Standards, special publication 314, November 1969, Library of Congress Card No. 79-601302. The book discusses ion-selective electrodes, some of which use gas permeable diffusion barriers, that would be operative in the systems of the present application.

Additional species of probes having multifunctional electrode systems based on the broad concepts of the present application are described in copending applications which are assigned to the same assignee as the present invention and are identified as follows: Ser. No. 519,796, naming John F. Brown, Jr. as inventor; Ser. No. 519,794, naming L. W. Niedrach and W. H. Stoddard, Jr. as inventors; Ser. No. 519,795, naming L. W. Niedrach and W. H. Stoddard, Jr. as inventors; Ser. No. 519,798, naming O. H. LeBlanc, W. T. Grubb and R. A. Macur as inventors; and Ser. No. 519,797, naming L. W. Niedrach and W. H. Stoddard, Jr. as inventors. All of said applications have the same filing date as this application. All of said applications are incorporated herein by reference.

I claim:

1. A unitary multifunctional probe for simultaneously determining the quantities of selected ion and gas constituents in a sample, comprising:
   a. first electrode means including an elongated member having an electrochemically active first electrode portion for producing a potential in response to and representative of the amount of one of said constituents in said sample when said electrochemically active first electrode portion is in electrochemical communication with said sample,
   b. second electrode means having an electrochemically active second electrode portion for producing a second potential in response to and representative of the amount of another of said constituents in said sample, which is different than said one constituent, when said second electrode portion is in electrochemical communication with said sample, said second electrode means being supported from said elongated member, and
   c. insulating means interposed between said first and second electrode means for isolating said first and second electrode means from each other,
   d. at least one of said electrode means including a reference electrode having an electrochemically active portion in insulating spaced relationship relative to an aforesaid electrochemically active portion, said reference electrode being supported insulatingly from said elongated member and cooperating with at least one of said electrochemically active portion to produce a potential which is representative of a constituent,
   e. an electrolyte in mutual contact with said reference electrode active portion and with said active portion of said at least one electrode means, and
   f. a diffusion barrier enclosing said electrolyte,
   g. said second electrode means including a second reference electrode having an electrochemically active portion in insulating spaced relationship relative to its cooperating one of said electrochemically active portions, said second reference electrode being supported insulatingly from said elongated member, h. an electrolyte in mutual contact with said active portion of said second reference electrode and the active portion of its cooperating electrode.

2. A unitary multifunctional probe for enabling simultaneous independent sensing of selected ion and gas constituents in a sample comprising:

a. an elongated first conductive member having one end for connecting to an electrical measuring circuit, b. plural electrode means responsive selectively to ion and gas constituents when said electrode means are inserted in a sample with predetermined ions and gases therein, c. one of said electrode means including a first electrochemically active region on said conductive member remote from said one end, said active region participating in producing a first potential representative of the amount of a first constituent in said sample when said electrode means is in electrochemical communication with a sample, d. said one electrode means also including a reference electrode having an active region insulated from and spaced from said first electrochemically active region and participating therewith to produce said first potential, d. another electrode means including a second elongated conductive means having one end for connecting to an electrical measuring circuit and supported from and insulated from said first conductive member, an electrochemically active region on said second conductive means, said last named electrochemically active region participating in producing another potential representative of the amount of another constituent, which is different than said first constituent, when said another electrode means is in electrochemical communication with a sample, f. said another electrode means also including a reference electrode having an active region insulated from the said electrochemically active region on said second conductive means and participating therewith to produce said another potential, g. insulating means interposed between said one and said another electrode means for isolating said first and second means against electrochemical interaction, h. insulating means for isolating said second electrode means from a sample in which said probe is inserted, i. a constituent selective diffusion barrier encasing at least one of said electrode means, and j. an electrolyte inside of said barrier and in contact with at least one electrode means.

3. A unitary multifunctional probe for enabling independent simultaneous sensing of selected ion and gas constituents in a sample comprising:

a. an elongated first conductive means having one end for connecting to an electrical measuring circuit, b. plural electrode means for simultaneously producing potentials, respectively, representative of the amounts of different ion and gas constituents in said sample when said electrode means are inserted in a sample with predetermined ions and gases therein, c. one electrode means comprising a first electrochemically active region on said elongated first conductive means remote from said one end, said active region being for producing a first potential representative of a first constituent in said sample when said electrode means is in electrochemical communication with a sample, d. another electrode means comprising a second elongated conductive means having one end for connecting to an electrical measuring circuit and supported from and insulated from said first elongated conductive means, an electrochemically active region on said second conductive means, said last named electrochemically active region being for producing another potential representative of another constituent when said another electrode means is in electrochemical communication with a sample, e. insulating means interposed between said one and said another electrode means for isolating said electrode means against electrochemical interaction and permitting independent function thereof, f. insulating means for isolating said second electrode means from a sample in which said probe is inserted, g. a constituent selective diffusion barrier encasing one of said electrode means, and h. an electrolyte inside of said barrier and in contact with said last named electrode means, i. said first electrochemically active region in said first electrode means being a metal selected from the group consisting of tungsten, molybdenum and tantalum, said region being sensitive to oxygen, j. a silver-silver halide, other than fluoride, reference electrode insulatingly spaced from said first electrochemically active region, and elongated conductive means extending from said reference electrode for connecting to an electrical measuring circuit outside of said probe, k. an electrolyte in contact with said oxygen sensitive electrochemically active region and with said silver halide reference electrode, and l. said diffusion barrier encasing said electrolyte and said reference electrode and said oxygen sensitive region, said diffusion barrier being permeable to a selected ion and to oxygen, m. said electrochemically active region of said second electrode means being sensitive to carbon dioxide and comprising a metal and an oxide of the same metal, said metal being selected from the group consisting of palladium and iridium, n. another silver-silver halide reference electrode insulatingly spaced from said last named electrochemically active region and elongated conductive means extending from said last named reference electrode for connecting to an electrical measuring circuit outside of said probe, o. another electrolyte in contact with said another carbon dioxide sensitive electrochemically active region and with said another reference electrode, and p. a diffusion barrier encasing said carbon dioxide sensitive electrode and said another reference electrode and said another electrolyte, said barrier being permeable to at least carbon dioxide.

4. The probe as in claim 3 wherein said another electrolyte is an aqueous solution containing bicarbonate and halide ions.

5. A unitary multifunctional probe for enabling simultaneous selective sensing of ion and gas constituents in a sample comprising:
a. one and another conductive means,
b. cooperating electrochemically active regions on each of said conductive means,
c. means for insulating said electrochemically active regions from each other,
d. an electrolyte contacting said electrochemically active regions,
e. a diffusion barrier material permeable to at least one of said constituents and encasing said electrolyte,
f. a second electrochemically active region on said another of said conductive means spaced from its aforesaid electrochemically active region,
g. means for isolating said second electrochemically active region from said electrolyte,
h. third conductive means having an electrochemically active region thereon, and
i. means for insulating said electrochemically active region on said third conductive means from said second electrochemically active region on said another conductive means.

6. The probe in claim 5 wherein:
a. said electrochemically active regions on said another conductive means comprise silver-silver halide reference electrodes, said active region on said one of said conductive means responding to oxygen in conjunction with one of said reference electrodes,
b. said electrochemically active region on said third conductive means responding to carbon dioxide in conjunction with said other reference electrode,
c. said last named electrochemically active regions having an electrolyte in mutual contact therewith and a carbon dioxide permeable diffusion barrier encasing said electrolyte,
d. the first named diffusion barrier being permeable to oxygen and a predetermined ion.

7. The probe in claim 6 wherein:
a. said oxygen responsive electrochemically active region cooperating with said one reference electrode is a metal selected from the group consisting of tantalum, molybdenum and tungsten, said reference electrode also being responsive to ions which permeate said diffusion barrier, and
b. said carbon dioxide responsive electrochemically active region cooperating with said other reference electrode is a metal selected from the group consisting of palladium and irridum with an oxide coating of the selected metal thereon.

8. The probe in claim 7 wherein:
a. said diffusion barrier which is permeable to carbon dioxide comprises silicone polycarbonate block copolymer.

9. The probe in claim 7 wherein:
a. said diffusion barrier which is permeable to oxygen and hydrogen ions comprises a hydrophobic elastomer-polymer with a dielectric constant of from 4 to 13, and a hydrogen ion carrier which is an uncoupler known to uncouple phosphorylation in mitochondria chloroplasts, said uncoupler being rendered hydrophobic and lipophilic.

10. A unitary multifunctional probe for enabling simultaneous sensing of hydrogen ions and carbon dioxide and oxygen gases, comprising:
a. a plurality of elongated conductive means having proximal ends providing means for connecting to electrical measuring circuits external to the probe,
b. a plurality of electrode systems comprising adjacent electrodes responsive to selected gases and ions and to combinations thereof, said electrodes being in conductive relation to said elongated conductive means, respectively,
c. one of said systems being responsive to oxygen gas and hydrogen ions and the other of said systems being responsive to carbon dioxide gas,
d. said one system which is responsive to oxygen gas and hydrogen ions comprising a first electrode having an electrochemically active region composed of a metal selected from the group consisting of molybdenum, tantalum and tungsten,
e. a second electrode in said one system in insulated spaced relation to said first electrode, said second electrode having an electrochemically active region composed of silver-silver halide other than fluoride,
f. another of said electrode systems which is responsive to carbon dioxide comprising a third electrode having an electrochemically active region composed of silver-silver halide other than fluoride,
g. a fourth electrode in said another system in insulated spaced relation to said third electrode, said fourth electrode having an electrochemically active region composed of a metal selected from the group consisting of palladium and iridium having the oxide, respectively, of said metal coated thereon,
h. insulating means interposed between said electrode systems,
i. an electrolyte in mutual contact with said first and second electrodes and an oxygen gas and hydrogen ion permeable diffusion barrier encasing said electrolyte and said first and second electrodes,
j. an electrolyte in mutual contact with said third and fourth electrodes and a diffusion barrier at least permeable to carbon dioxide encasing said last named electrolyte and said third and fourth electrodes,
k. said last named barrier means also serving as insulating means extending toward said proximal end,
l. potentials measured externally of said probe between said first and second electrodes indicating the partial pressure of oxygen in said sample, the potential measured from an external electrode, which is in ionic communication with said sample, across said barrier to said second electrode indicating the hydrogen ion level of said sample and the potential measured between said third and fourth electrodes indicating the partial pressure of carbon dioxide in said sample.

11. The probe in claim 10 wherein:
a. said carbon dioxide permeable diffusion barrier comprises organo-polysiloxane polycarbonate block copolymer.

12. The probe in claim 10 wherein:
a. said electrolyte in contact with said third and fourth electrodes is an aqueous solution including bicarbonate ions and halide ions other than fluoride ions.

13. The probe in claim 10 wherein:
a. said oxygen and hydrogen ion permeable diffusion barrier is comprised of a hydrophobic elastomer-polymer with a dielectric constant of 4 to 13, and a hydrogen ion carrier which is an uncoupler known to uncouple phosphorylation in mitochondria and chloroplasts, said uncoupler being rendered hydrophobic and lipophilic.

14. The probe in claim 10 wherein:
   a. said electrolyte in said contact with said first and second electrodes comprises an aqueous solution of halide ions other than fluoride ions and a buffer to establish said electrolyte at about pH 5.

15. A unitary probe for determining the partial pressures of carbon dioxide and oxygen in a sample and the pH thereof, comprising:
   a. a central elongated wire comprising metal selected from the group of molybdenum, tantalum and tungsten,
   b. a first insulating layer surrounding said wire excluding a tip region thereof which region constitutes an electrode sensitive to oxygen,
   c. a substantially silver layer surrounding said first insulating layer, said silver layer having at least two regions thereon coated with silver halide, excluding fluoride, said coated regions constituting first and second reference electrodes, said tip region electrode cooperating with said first reference electrode to sense oxygen,
   d. a second insulating layer surrounding said silver layer for separating said halide coated reference electrode regions,
   e. a third insulating layer surrounding said silver layer such that said second halide coated reference electrode region is exposed between said second and third insulating layers,
   f. a layer of metal selected from the group consisting of palladium and iridium surrounding said third insulating layer and having an end region comprising an electrode coated with an oxide of the selected metal which region is spaced from said second reference electrode by said third insulating layer, said second reference electrode and said oxide coated electrode cooperating to sense carbon dioxide,
   g. an electrolyte including halide ions and a buffer in mutual contact with said tip region and said first reference electrode, said buffer establishing said electrolyte at about pH 5,
   h. an oxygen gas and hydrogen ion permeable diffusion barrier encasing said electrolyte,
   i. an electrolyte in mutual contact with said second reference electrode and said oxide coated electrode and carbon dioxide gas permeable diffusion barrier encasing said last mentioned electrolyte, and
   j. an insulating layer extending over said probe continuously from said last named diffusion barrier,
   k. a potential measured externally of said probe between said electrode tip and said first reference electrode being indicative of the partial pressure of oxygen in said sample, a potential measured externally of said probe between said first reference electrode internal to said barrier and another external reference electrode that is in communication with said sample being indicative of the pH of said sample, and the potential measured externally of said probe between said second reference electrode and said oxide coated electrode being indicative of the partial pressure of carbon dioxide gas in said sample.

* * * * *